United States Patent [19]
Hulsink

[11] Patent Number: 4,516,936
[45] Date of Patent: May 14, 1985

[54] ORTHODONTIC DEVICE

[76] Inventor: Jan H. Hulsink, Zuylensteinseweg 19, 3958 BA Amerongen, Netherlands

[21] Appl. No.: 494,180

[22] Filed: May 13, 1983

[30] Foreign Application Priority Data

Mar. 4, 1983 [NL] Netherlands .......... 8300810

[51] Int. Cl.³ .............................. A61C 3/00
[52] U.S. Cl. ...................................... 433/6
[58] Field of Search .............. 433/6, 7, 18, 19, 24

[56] References Cited

U.S. PATENT DOCUMENTS

| | | | |
|---|---|---|---|
| 646,629 | 4/1900 | Sugatt | 433/6 |
| 3,295,519 | 1/1967 | Gerber | 433/6 |
| 3,849,885 | 11/1974 | Robins | 433/6 |
| 4,224,021 | 9/1980 | Foxman | 433/18 |
| 4,253,828 | 3/1981 | Coles et al. | 433/6 |
| 4,299,568 | 11/1981 | Crowley | 433/6 |
| 4,413,978 | 11/1983 | Kurz | 433/6 |
| 4,468,196 | 8/1984 | Keller | 433/7 |

FOREIGN PATENT DOCUMENTS

| | | | |
|---|---|---|---|
| 1293946 | 4/1969 | Fed. Rep. of Germany | 433/6 |
| 785198 | 8/1935 | France | 433/7 |
| 7903644 | 11/1979 | Netherlands | 433/6 |
| 972761 | 10/1964 | United Kingdom | 433/18 |

Primary Examiner—John J. Wilson
Attorney, Agent, or Firm—Lee, Smith & Zickert

[57] ABSTRACT

An orthodontic device comprises a dental plate from plastic or the like adapted to be fitted to the jaw. One or more wire clamps may be fixed to the dental plate along its side edges and destined to be positioned around and/or between at least a number of molar teeth. An anchor is fixed to the dental plate along its front edge and destined to grip in fitting relation around at least a number of teeth. The anchor is formed from colorless transparent plastic that is connected integrally to the dental plate and fits closely against the front and rear side of all of the teeth of the jaw. At least the cutting faces of the incisors project freely through the anchor.

7 Claims, 2 Drawing Figures

ORTHODONTIC DEVICE

BACKGROUND OF THE INVENTION

The invention relates to an orthodontic device comprising a dental plate formed from plastic or the like and adapted to fit the jaw. For example, The plate may have along its side edges one or more wire clamps fixed thereto and destined to be positioned around and/or between at least a number of molar teeth and along the front edge, anchoring means fixed to the dental plate and destined to grip fittingly around at least a number of teeth.

Such devices are known in practice and literature, (see for example FIG. 1 of the Dutch Patent Application No. 79 03644) and are used in particular for straightening children's teeth. Instead of wire clamps other means may be used.

The principle of such devices is that from a fixed anchoring means, the lateral elements such as cuspidati, praemolars and molars are displaced to distal or to mesial by means of wire clamps.

In practice as anchoring means, a wire clamp is generally used gripping fittingly around a number of front elements. The front edge of the dental plate presses against the rear side of the front elements. Said known device has several disadvantages.

In the first instance, the device should be made fitting in the mouth of the patient by the doctor and thereafter should be touched up once again outside of the mouth. This is inconvenient for the patient and the treatment is naturally extremely expensive.

Further, the risk of loss of anchoring is very high.

Another objection is the less finer appearance of the known devices because of the visible wire clamp around the front side of the front elements. Moreover, problems often arise with the lips of the patient because the wire clamp is relatively thick, approximately 2–3 mm.

SUMMARY OF THE INVENTION

The object of the invention is to improve the known device. This is achieved according to the invention in that the anchoring means is formed from colorless transparent plastics connected integrally to the dental plate and fitting closely against the front and rear side of all of the teeth of the jaw, in which at least the cutting faces of the incisors project freely through the anchoring means.

From the jaw of the patient, a model is made with known means, after which the anchoring means may be shaped in the laboratory to fit around the front elements of the model. Preferably, the anchoring means is shaped by known vacuum or overpressure techniques from a plate of plastic material corresponding to the shape of the teeth or other front elements.

In a known way, the dental plate may be formed with wire clamps being eventually connected thereto. The plate may then be connected to the anchoring means to form a single piece.

The invention relates also to only anchoring means intended to be used in an orthodontic device.

BRIEF DESCRIPTION OF THE DRAWING

Now as an example, the invention will be described in detail by reference to the drawing in which.

DESCRIPTION OF THE PREFERRED EMBODIMENT

As an example and in a known way, the jaw model is formed from plaster or the like and represents in addition to the shape of the palate, also the molar teeth and teeth of the patient.

From a transparent plastic plate, for example from polycarbonate, first the anchoring means 1 is shaped to now correspond to the shape of the front elements and the front portion of the palate. The limitation line of the anchoring means 1 against the plate is indicated by 2.

Figure 1:
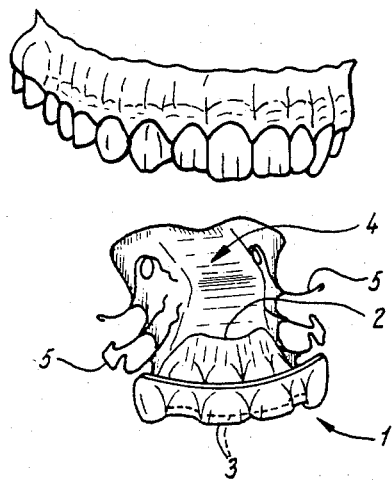
FIG. 1 is a perspective view of a portion of the jaw model with a top view of an orthodontic device according to the invention.

Shaping of the plastic plate may be carried out by known vacuum or overpressure techniques, by which the plate engages completely against the model. Thereafter, the shaped plate is finished, in which at the same time at the location of the cutting faces of the incisors, the plate is removed so that the cutting faces project through the location indicated by dashed line 3 in FIG. 1 and in the bottom view by 3 In FIG. 2.

Figure 2:
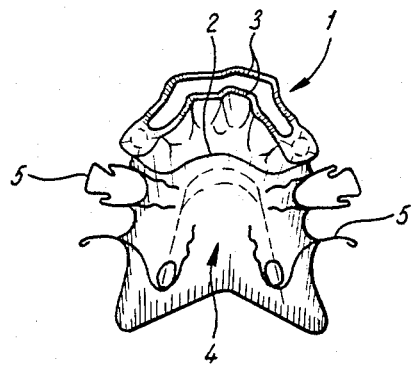
FIG. 2 is a bottom view of said orthodontic device.

From FIG. 2 it appears clearly that the anchoring means thus shaped fits closely at its inner and its outer side against the four incisors and grips fittingly around both of the eye-teeth. Self-evidently, also one or more front elements may be lacking. Any way, a very firm anchoring is produced for the orthodontic device which may be manufactured in completely fitting relation to the model. At the front side of the set of teeth, only either a small portion or none of the anchoring means is visible, and the functioning of the incisors is not adversely affected.

After shaping the anchoring means, the dental plate 4 is moulded in known way, for example by powder technique, and the wire clamps 5 are eventually connected thereto. The line 2 represents the separation between the transparent anchoring means 1 and the dental plate 4 connected integrally thereto and being coloured generally.

Self-evidently, the anchoring means 1 may be applied to all kinds of orthodontic devices needing an anchoring to the front elements.

I claim:

1. An orthodontic device comprising, a dental plate adapted to be fitted to the jaw, wire clamp means extending from the side edges of said dental plate for engagement with at least one tooth to apply moving forces to the teeth, and anchoring means extending from the front of said plate adapted to grippingly fit about the front and rear surfaces of a plurality of anterior teeth, said anchoring means being formed entirely from a colorless transparent plastic and being shaped to complementally fit closely against the front and rear surfaces of the anterior teeth and to have an opening through which at least some of the cutting faces of the incisors may freely project.

2. The device of claim 1, wherein said dental plate is of colorless transparent plastic.

3. The device of claim 1, wherein said clamp means is adapted to engage at least a molar tooth on each side of said plates.

4. The device of claim 1, wherein said anchoring means is formed to cover substantially all of the front and rear surfaces of said anterior teeth.

5. The device of claim 1, wherein said dental plate is adapted to be fitted to the upper jaw and to the palate and the lingual surfaces of the teeth.

6. An orthodontic device for the jaw comprising, a plastic dental plate adapted to be fitted to the jaw and the lingual surfaces of the teeth to apply moving forces to the teeth, wire clamp means extending from the sides of said plate for engagement with the posterior teeth, anchoring means at the front of said plate adapted to grippingly fit about the front and rear surfaces of a plurality of anterior teeth, said anchoring means being formed completely from plastic and being shaped to complementally fit closely against substantially the entire front and rear surfaces of said anterior teeth and to have an opening through which at least the cutting faces of the central incisors may freely project.

7. The device of claim 6, wherein said plastic anchoring means is colorless.

* * * * *